US010716525B2

(12) United States Patent
Weingarten et al.

(10) Patent No.: US 10,716,525 B2
(45) Date of Patent: Jul. 21, 2020

(54) SYSTEM AND METHOD FOR NAVIGATING TO TARGET AND PERFORMING PROCEDURE ON TARGET UTILIZING FLUOROSCOPIC-BASED LOCAL THREE DIMENSIONAL VOLUME RECONSTRUCTION

(71) Applicant: COVIDIEN LP, Mansfield, MA (US)

(72) Inventors: Oren P. Weingarten, Herzliya (IL); Ron Barak, Herzliya (IL); Benjamin Greenburg, Hod Hasharon (IL); Eyal Klein, Herzliya (IL); Evgeni Kopel, Herzliya (IL)

(73) Assignee: Covidien LP, Mansfield, MA (US)

( * ) Notice: Subject to any disclaimer, the term of this patent is extended or adjusted under 35 U.S.C. 154(b) by 1025 days.

(21) Appl. No.: 15/224,898

(22) Filed: Aug. 1, 2016

(65) Prior Publication Data
US 2017/0035380 A1    Feb. 9, 2017

Related U.S. Application Data

(60) Provisional application No. 62/201,750, filed on Aug. 6, 2015.

(51) Int. Cl.
*A61B 5/05* (2006.01)
*A61B 6/00* (2006.01)
(Continued)

(52) U.S. Cl.
CPC .............. *A61B 6/487* (2013.01); *A61B 5/062* (2013.01); *A61B 6/12* (2013.01); *A61B 6/4405* (2013.01);
(Continued)

(58) Field of Classification Search
None
See application file for complete search history.

(56) References Cited

U.S. PATENT DOCUMENTS 5,852,646 A    12/1998    Klotz et al.
5,930,329 A    7/1999    Navab
(Continued)

FOREIGN PATENT DOCUMENTS

CN    101190149 A    6/2008
JP    11197259    7/1999
(Continued)

OTHER PUBLICATIONS

Extended European Search Report from Appl. No. EP 16182953.6-1666 dated Jan. 2, 2017.
(Continued)

*Primary Examiner* — Joel F Brutus

(57) ABSTRACT

A system and method for navigating to a target using fluoroscopic-based three dimensional volumetric data generated from two dimensional fluoroscopic images, including a catheter guide assembly including a sensor, an electromagnetic field generator, a fluoroscopic imaging device to acquire a fluoroscopic video of a target area about a plurality of angles relative to the target area, and a computing device. The computing device is configured to receive previously acquired CT data, determine the location of the sensor based on the electromagnetic field generated by the electromagnetic field generator, generate a three dimensional rendering of the target area based on the acquired fluoroscopic video, receive a selection of the catheter guide assembly in the generated three dimensional rendering, and register the generated three dimensional rendering of the target area with the previously acquired CT data to correct the position of the catheter guide assembly.

16 Claims, 4 Drawing Sheets

(51) Int. Cl.
*A61B 5/06* (2006.01)
*A61B 34/10* (2016.01)
*A61B 34/20* (2016.01)
*A61B 6/12* (2006.01)
*A61B 90/00* (2016.01)
*A61B 17/00* (2006.01)

(52) U.S. Cl.
CPC ............ *A61B 6/4441* (2013.01); *A61B 6/466* (2013.01); *A61B 6/5205* (2013.01); *A61B 34/10* (2016.02); *A61B 34/20* (2016.02); *A61B 2017/00809* (2013.01); *A61B 2034/105* (2016.02); *A61B 2034/2051* (2016.02); *A61B 2090/367* (2016.02); *A61B 2090/3764* (2016.02); *A61B 2090/3966* (2016.02)

(56) References Cited

U.S. PATENT DOCUMENTS

| | | |
|---|---|---|
| 5,963,612 A | 10/1999 | Navab |
| 5,963,613 A | 10/1999 | Navab |
| 6,038,282 A | 3/2000 | Wiesent et al. |
| 6,049,582 A | 4/2000 | Navab |
| 6,050,724 A | 4/2000 | Schmitz et al. |
| 6,055,449 A | 4/2000 | Navab |
| 6,081,577 A | 6/2000 | Webber |
| 6,120,180 A | 9/2000 | Graumann |
| 6,236,704 B1 | 5/2001 | Navab et al. |
| 6,317,621 B1 | 11/2001 | Graumann et al. |
| 6,351,513 B1 | 2/2002 | Bani-Hashemi et al. |
| 6,389,104 B1 | 5/2002 | Bani-Hashemi et al. |
| 6,404,843 B1 | 6/2002 | Valliant |
| 6,424,731 B1 | 7/2002 | Launay et al. |
| 6,484,049 B1 | 11/2002 | Seeley et al. |
| 6,485,422 B1 | 11/2002 | Mikus et al. |
| 6,490,475 B1 | 12/2002 | Seeley et al. |
| 6,491,430 B1 | 12/2002 | Seissler |
| 6,546,068 B1 | 4/2003 | Shimura |
| 6,546,279 B1 | 4/2003 | Bova et al. |
| 6,549,607 B1 | 4/2003 | Webber |
| 6,697,664 B2 | 2/2004 | Kienzle, III et al. |
| 6,707,878 B2 | 3/2004 | Claus et al. |
| 6,714,810 B2 | 3/2004 | Grzeszczuk et al. |
| 6,731,283 B1 | 5/2004 | Navab |
| 6,731,970 B2 | 5/2004 | Schlossbauer et al. |
| 6,768,784 B1 | 7/2004 | Green et al. |
| 6,782,287 B2 | 8/2004 | Grzeszczuk et al. |
| 6,785,356 B2 | 8/2004 | Grass et al. |
| 6,785,571 B2 | 8/2004 | Glossop |
| 6,801,597 B2 | 10/2004 | Webber |
| 6,823,207 B1 | 11/2004 | Jensen et al. |
| 6,856,826 B2 | 2/2005 | Seeley et al. |
| 6,856,827 B2 | 2/2005 | Seeley et al. |
| 6,865,253 B2 | 3/2005 | Blumhofer et al. |
| 6,898,263 B2 | 5/2005 | Avinash et al. |
| 6,944,260 B2 | 9/2005 | Hsieh et al. |
| 6,956,927 B2 | 10/2005 | Sukeyasu et al. |
| 7,010,080 B2 | 3/2006 | Mitschke et al. |
| 7,010,152 B2 | 3/2006 | Bojer et al. |
| 7,035,371 B2 | 4/2006 | Boese et al. |
| 7,106,825 B2 | 9/2006 | Gregerson et al. |
| 7,117,027 B2 | 10/2006 | Zheng et al. |
| 7,129,946 B2 | 10/2006 | Ditt et al. |
| 7,130,676 B2 | 10/2006 | Barrick |
| 7,165,362 B2 | 1/2007 | Jobs et al. |
| 7,251,522 B2 | 7/2007 | Essenreiter et al. |
| 7,327,872 B2 | 2/2008 | Vaillant et al. |
| 7,343,195 B2 | 3/2008 | Strommer et al. |
| 7,369,641 B2 | 5/2008 | Tsubaki et al. |
| 7,440,538 B2 | 10/2008 | Tsujii |
| 7,467,007 B2 | 12/2008 | Lothert |
| 7,474,913 B2 | 1/2009 | Durlak |
| 7,502,503 B2 | 3/2009 | Bojer et al. |
| 7,505,549 B2 | 3/2009 | Ohishi et al. |
| 7,508,388 B2 | 3/2009 | Barfuss et al. |
| 7,603,155 B2 | 10/2009 | Jensen |
| 7,620,223 B2 | 11/2009 | Xu et al. |
| 7,639,866 B2 | 12/2009 | Pomero et al. |
| 7,664,542 B2 | 2/2010 | Boese et al. |
| 7,689,019 B2 | 3/2010 | Boese et al. |
| 7,689,042 B2 | 3/2010 | Brunner et al. |
| 7,693,263 B2 | 4/2010 | Bouvier et al. |
| 7,711,082 B2 | 5/2010 | Fujimoto et al. |
| 7,711,083 B2 | 5/2010 | Heigl et al. |
| 7,711,409 B2 | 5/2010 | Keppel et al. |
| 7,720,520 B2 | 5/2010 | Willis |
| 7,725,165 B2 | 5/2010 | Chen et al. |
| 7,734,329 B2 | 6/2010 | Boese et al. |
| 7,742,557 B2 | 6/2010 | Brunner et al. |
| 7,761,135 B2 | 7/2010 | Pfister et al. |
| 7,778,685 B2 | 8/2010 | Evron et al. |
| 7,787,932 B2 | 8/2010 | Vilsmeier et al. |
| 7,804,991 B2 | 9/2010 | Abovitz et al. |
| 7,831,096 B2 | 11/2010 | Williamson, Jr. |
| 7,835,779 B2 | 11/2010 | Anderson et al. |
| 7,853,061 B2 | 12/2010 | Gorges et al. |
| 7,877,132 B2 | 1/2011 | Rongen et al. |
| 7,899,226 B2 | 3/2011 | Pescatore et al. |
| 7,907,989 B2 | 3/2011 | Borgert et al. |
| 7,912,180 B2 | 3/2011 | Zou et al. |
| 7,912,262 B2 | 3/2011 | Timmer et al. |
| 7,949,088 B2 | 5/2011 | Nishide et al. |
| 7,991,450 B2 | 8/2011 | Virtue et al. |
| 8,000,436 B2 | 8/2011 | Seppi et al. |
| 8,043,003 B2 | 10/2011 | Vogt et al. |
| 8,045,780 B2 | 10/2011 | Boese et al. |
| 8,050,739 B2 | 11/2011 | Eck et al. |
| 8,090,168 B2 | 1/2012 | Washburn et al. |
| 8,111,894 B2 | 2/2012 | Van De Haar |
| 8,111,895 B2 | 2/2012 | Spahn |
| 8,126,111 B2 | 2/2012 | Uhde et al. |
| 8,126,241 B2 | 2/2012 | Zarkh et al. |
| 8,150,131 B2 | 4/2012 | Harer et al. |
| 8,180,132 B2 | 5/2012 | Gorges et al. |
| 8,195,271 B2 | 6/2012 | Rahn |
| 8,200,316 B2 | 6/2012 | Keppel et al. |
| 8,208,708 B2 | 6/2012 | Homan et al. |
| 8,229,061 B2 | 7/2012 | Hanke et al. |
| 8,248,413 B2 | 8/2012 | Gattani et al. |
| 8,270,691 B2 | 9/2012 | Xu et al. |
| 8,271,068 B2 | 9/2012 | Khamene et al. |
| 8,275,448 B2 | 9/2012 | Camus et al. |
| 8,306,303 B2 | 11/2012 | Bruder et al. |
| 8,311,617 B2 | 11/2012 | Keppel et al. |
| 8,320,992 B2 | 11/2012 | Frenkel et al. |
| 8,340,379 B2 | 12/2012 | Razzaque et al. |
| 8,345,817 B2 | 1/2013 | Fuchs et al. |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,515,527 B2 | 8/2013 | Valliant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,831,310 B2 | 9/2014 | Razzaque et al. |
| 8,855,748 B2 | 10/2014 | Keppel et al. |

(56) References Cited

U.S. PATENT DOCUMENTS

| | | |
|---|---|---|
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,401,047 B2 | 7/2016 | Bogoni et al. |
| 9,406,134 B2 | 8/2016 | Klingenbeck-Regn |
| 9,445,772 B2 | 9/2016 | Callaghan |
| 9,445,776 B2 | 9/2016 | Han et al. |
| 9,466,135 B2 | 10/2016 | Koehler et al. |
| 9,743,896 B2 | 8/2017 | Averbuch |
| 2003/0088179 A1* | 5/2003 | Seeley .................. A61B 6/12 600/424 |
| 2003/0208122 A1* | 11/2003 | Melkent .................. A61B 5/06 600/426 |
| 2006/0251213 A1 | 11/2006 | Bernhardt et al. |
| 2012/0289825 A1* | 11/2012 | Rai .......................... A61B 6/12 600/425 |
| 2014/0100440 A1* | 4/2014 | Cheline .............. A61B 5/02007 600/407 |
| 2015/0227679 A1 | 8/2015 | Kamer et al. |
| 2016/0005194 A1 | 1/2016 | Schretter et al. |
| 2016/0206380 A1 | 7/2016 | Sparks et al. |
| 2016/0287343 A1 | 10/2016 | Eichler et al. |

FOREIGN PATENT DOCUMENTS

| | | |
|---|---|---|
| WO | 2008038283 A2 | 4/2008 |
| WO | 2009081297 A2 | 7/2009 |
| WO | 2014186715 A1 | 11/2014 |
| WO | 2015101948 A2 | 7/2015 |

OTHER PUBLICATIONS

CT scan—Wikipedia, the free encyclopedia [retrieved from internet on Mar. 30, 2017]. <URL:http://web.archive.org/web/20150630170453/https://en.wikipedia.org/wiki/CT_scan> published on Jun. 30, 2015 as per Wayback Machine.

Australian Examination Report No. 2 issued in Appl. No. AU 2016210747 dated Oct. 18, 2017 (4 pages).

Office Action issued in Chinese Appl. No. 201610635896.X dated Jul. 23, 2018, together with English language translation (16 pages).

Japanese Office Action issued in Appl. No. JP 2019-021423, together with English language translation, dated Jan. 8, 2020 (7 pages).

* cited by examiner

SYSTEM AND METHOD FOR NAVIGATING TO TARGET AND PERFORMING PROCEDURE ON TARGET UTILIZING FLUOROSCOPIC-BASED LOCAL THREE DIMENSIONAL VOLUME RECONSTRUCTION

CROSS-REFERENCE TO RELATED APPLICATIONS

This application claims priority to U.S. Provisional Application Ser. No. 62/201,750, filed on Aug. 6, 2015, the entire content of which is incorporated by reference herein.

BACKGROUND

Technical Field

The present disclosure relates to a system, apparatus, and method of navigation and position confirmation for surgical procedures. More particularly, the present disclosure relates to a system and method for enhanced navigation of a catheter and one or more medical instruments positionable therethrough in one or more branched luminal networks of a patient and confirming placement of those medical instruments prior to initiating treatment or biopsy based on a three dimensional computed tomography volume generated from standard fluoroscopic images.

Description of Related Art

There are several commonly applied methods for treating various maladies affecting organs including the liver, brain, heart, lung and kidney. Often, one or more imaging modalities, such as magnetic resonance imaging, ultrasound imaging, computer tomography (CT), as well as others are employed by clinicians to identify areas of interest within a patient and ultimately targets for treatment.

An endoscopic approach has proven useful in navigating to areas of interest within a patient, and particularly so for areas within luminal networks of the body such as the lungs. To enable the endoscopic, and more particularly the bronchoscopic, approach in the lungs, endobronchial navigation systems have been developed that use previously acquired MRI data or CT image data to generate a three dimensional rendering or volume of the particular body part such as the lungs. In particular, previously acquired images, acquired from an MRI scan or CT scan of the patient, are utilized to generate a three dimensional or volumetric rendering of the patient.

The resulting volume generated from the MRI scan or CT scan is then utilized to create a navigation plan to facilitate the advancement of a navigation catheter (or other suitable device) through a bronchoscope and a branch of the bronchus of a patient to an area of interest. Electromagnetic tracking may be utilized in conjunction with the CT data to facilitate guidance of the navigation catheter through the branch of the bronchus to the area of interest. In certain instances, the navigation catheter may be positioned within one of the airways of the branched luminal networks adjacent to, or within, the area of interest to provide access for one or more medical instruments.

Thus, in order to generate a navigation plan, or in order to even generate a three dimensional or volumetric rendering of the patient's anatomy, such as the lung, a clinician is required to utilize an MRI system or CT system to acquire the necessary image data for construction of the three dimensional volume. It would be ideal to utilize an MRI system or CT-based imaging system, like that of which is used during the planning phase to generate a volumetric rendering, during the procedure to generate near real-time data during the procedure. However such an MRI system of CT-based imaging system is extremely costly, and in many cases not available in the same location as the location where a navigation procedure is carried out. Additionally, such systems expose patients to high doses of radiation, thus making it desirable to reduce a patient's exposure as much as possible.

A fluoroscopic imaging device is commonly located in the operating room during navigation procedures. The standard fluoroscopic imaging device may be used by a clinician to visualize and confirm the placement of a tool after it has been navigated to a desired location. However, although standard fluoroscopic images display highly dense objects such as metal tools and bones as well as large soft-tissue objects such as the heart, the fluoroscopic images have difficulty resolving small soft-tissue objects of interest such as lesions. Further, the fluoroscope image is only a two dimensional projection. In order to be able to see small soft-tissue objects in three dimensional space, an X-ray volumetric reconstruction is needed. Several solutions exist that provide three dimensional volume reconstruction of soft-tissues such as CT and Cone-beam CT which are extensively used in the medical world. These machines algorithmically combine multiple X-ray projections from known, calibrated X-ray source positions into three dimensional volume in which the soft-tissues are visible.

In order to navigate tools to a remote soft-tissue target for biopsy or treatment, both the tool and the target should be visible in some sort of a three dimensional guidance system. The majority of these systems use some X-ray device to see through the body. For example, a CT machine can be used with iterative scans during procedure to provide guidance through the body until the tools reach the target. This is a tedious procedure as it requires several full CT scans, a dedicated CT room and blind navigation between scans. In addition, each scan requires the staff to leave the room to avoid high radiation exposure. Another option is a Cone-beam CT machine which is available in some operation rooms and is somewhat easier to operate, but is expensive and like the CT only provides blind navigation between scans, requires multiple iterations for navigation and requires the staff to leave the room.

Accordingly, there is a need for a system that can achieve the benefits of the CT and Cone-beam CT three dimensional image guidance without the underlying costs, preparation requirements, and radiation side effects associated with these systems.

SUMMARY

The present disclosure is directed to a system and method for enhanced navigation of a catheter within a luminal network of a patient using local three dimensional volumetric data in which small soft-tissue objects are visible constructed from a fluoroscopic video stream, composed of a series of fluoroscopic images, captured by a standard fluoroscopic imaging device available in most procedure rooms. The fluoroscopic-based constructed local three dimensional volumetric data may be used for guidance, navigation planning, improved navigation accuracy, navigation confirmation, and treatment confirmation. In particular, one aspect of the present disclosure utilizes fluoroscopic images (or fluoroscopic video) in order to improve the accuracy of navigation during an electromagnetic navigation procedure (or other navigation procedure) and in order to confirm placement of a surgical tool(s) during such procedures.

Aspects of the present disclosure are described in detail with reference to the figures wherein like reference numerals identify similar or identical elements. As used herein, the term "distal" refers to the portion that is being described which is further from a user, while the term "proximal" refers to the portion that is being described which is closer to a user.

According to one aspect of the present disclosure, a system for navigating to a target using fluoroscopic-based three dimensional volumetric data generated from two dimensional fluoroscopic images is provided. The system includes a catheter guide assembly including a sensor disposed thereon, an electromagnetic field generator configured to generate an electromagnetic field for determining a location of the sensor, a fluoroscopic imaging device configured to acquire a fluoroscopic video of a target area about a plurality of angles relative to the target area, and a computing device. The computing device is configured to receive previously acquired CT data, determine the location of the sensor based on the electromagnetic field generated by the electromagnetic field generator, and generate a three-dimensional rendering of the target area based on the acquired fluoroscopic video. The computing device may also be configured to display the generated three-dimensional rendering, receive a selection (either automatically or manually) of the catheter guide assembly and/or the target within the generated three-dimensional rendering, and register the generated three-dimensional rendering of the target area with the previously acquired CT data. The fluoroscopic video of the target area may include a rotation about the target area in the range of fifteen degrees to sixty degrees. For example, the fluoroscopic video of the target area may include a thirty degree rotation about the target area, where the area covered is fifteen degrees about each side of the target area or patient.

The registration of the generated three-dimensional rendering of the target area (which includes the surgical device navigated to the target area and the target within the target area) with the previously acquired CT data may be accomplished using image-based techniques, including but not limited to, mutual information techniques. The generated three-dimensional rendering of the target area can be registered globally to the previously acquired CT data or locally (in proximity of an area of interest within the target area, for example, the target). The registration of the generated three-dimensional rendering of the target area with the previously acquired CT data may be accomplished using a deep-learning based approach, including but not limited to, approaches where the system learns how to register the two different modalities based on a comparison between many different good and bad registrations.

The computing device may be further configured to display a position of the catheter guide assembly with respect to the previously acquired CT data based on the determined location of the sensor and update, or otherwise correct, the displayed position of the catheter guide assembly with respect to the previously acquired CT data based on the registration of the generated three-dimensional rendering of the target area with the previously acquired CT data. In aspects, the computing device is further configured to detect a portion of the catheter guide assembly and/or the target in the acquired fluoroscopic video, suggest the detected portion to a user, and receive a user command either accepting or rejecting the detection.

Additionally, the computing device may be further configured to track the two dimensional position or orientation of the catheter guide assembly or medical device navigated to the target region throughout the fluoroscopic video. The computing device may be further configured to reconstruct positions of the medical device throughout the fluoroscopic video using a structure-from-motion technique. The pose of the fluoroscopic imaging device for each frame of the fluoroscopic video may be determined based on the reconstructed positions. Additionally, or alternatively, the pose of the fluoroscopic imaging device for each frame of the fluoroscopic video may be determined based on an external angle measurement device, for example an accelerometer, coupled to the fluoroscopic imaging device.

In yet another aspect of the present disclosure a method for navigating to a target using fluoroscopic-based three dimensional volumetric data generated from two dimensional fluoroscopic images is provided. The method includes receiving previously acquired CT data, navigating a catheter guide assembly including a sensor disposed thereon to the target, generating an electromagnetic field, and determining a location of the sensor based on the generated electromagnetic field. The method further includes acquiring a fluoroscopic video of the target area about a plurality of angles relative to the target area using a fluoroscopic imaging device, generating a three-dimensional rendering of the target area based on the acquired fluoroscopic video, optionally displaying the generated three-dimensional rendering, receiving a selection of the catheter guide assembly within the generated three-dimensional rendering, and registering the generated three-dimensional rendering of the target area with the previously acquired CT data. The method may further include navigating a radio-opaque marker to the target area, wherein the radio-opaque marker is at least partially visible in the fluoroscopic video acquired.

Additionally, the method may further include displaying a position of the catheter guide assembly with respect to the previously acquired CT data based on the determined location of the sensor and updating, or otherwise correcting, the position of the catheter guide assembly with respect to the previously acquired CT data based on the registration of the generated three-dimensional rendering of the target area with the previously acquired CT data. Additionally, the method may further include detecting a portion of the catheter guide assembly and/or the target in the acquired fluoroscopic video and receiving a user command either accepting or rejecting the detection.

The positions of the medical device throughout the fluoroscopic video may be reconstructed using a structure-from-motion technique. The pose of the fluoroscopic imaging device for each frame of the fluoroscopic video may be determined based on the reconstructed positions. Additionally, or alternatively, the pose of the fluoroscopic imaging device for each frame of the fluoroscopic video may be determined based on an external angle measurement device, for example an accelerometer, coupled to the fluoroscopic imaging device.

In yet another aspect of the present disclosure a non-transitory computer readable storage medium is provided. The non-transitory computer readable storage medium includes instructions, which when executed, causes a system to perform any of the methods described herein.

BRIEF DESCRIPTION OF THE DRAWINGS

Various aspects and embodiments of the present disclosure are described hereinbelow with references to the drawings, wherein.

DETAILED DESCRIPTION

The present disclosure is directed to a system and method for enhanced navigation of a catheter within a luminal network of a patient using local three dimensional volumetric data in which small soft-tissue objects are visible constructed from a fluoroscopic video stream, composed of a series of fluoroscopic images, captured by a standard fluoroscopic imaging device available in most procedure rooms. The fluoroscopic-based constructed local three dimensional volumetric data is registered with previously acquired volumetric data used for creating a navigation plan and diagnosis. Additionally, the fluoroscopic-based constructed local three dimensional volumetric data may be used for guidance, navigation planning, improved navigation accuracy, navigation confirmation, and treatment confirmation.

The three dimensional model of a patient's lungs, generated from previously acquired CT scans, may not provide a basis sufficient for accurate guiding of medical instruments to a target during an electromagnetic navigation procedure. In certain instances, the inaccuracy is caused by deformation of the patient's lungs during the procedure relative to the lungs at the time of the acquisition of the previously acquired CT data. This deformation (CT-to-Body divergence) may be caused by many different factors, for example: sedation vs. no sedation, bronchoscope changing patient pose and also pushing the tissue, different lung volume because CT was in inhale while navigation is during breathing, different bed, day, etc. Thus, another imaging modality is necessary to visualize targets and/or a terminal bronchial branch, and enhance the electromagnetic navigation procedure by correcting the navigation during the procedure, enabling visualization of the target, and confirming placement of the surgical device during the procedure. For this purpose, the system described herein processes and converts image data captured by the fluoroscopic imaging device 110, as will be described in detail below. This fluoroscopic image data may be utilized to identify such targets and terminal bronchial branches or be incorporated into, and used to update, the data from the CT scans in an effort to provide a more accurate/correction of the electromagnetic navigation procedure. Further, the fluoroscopic images may be captured post-navigation and thus includes visuals of the position of the navigated medical instrument relative to the target.

Figure 1:
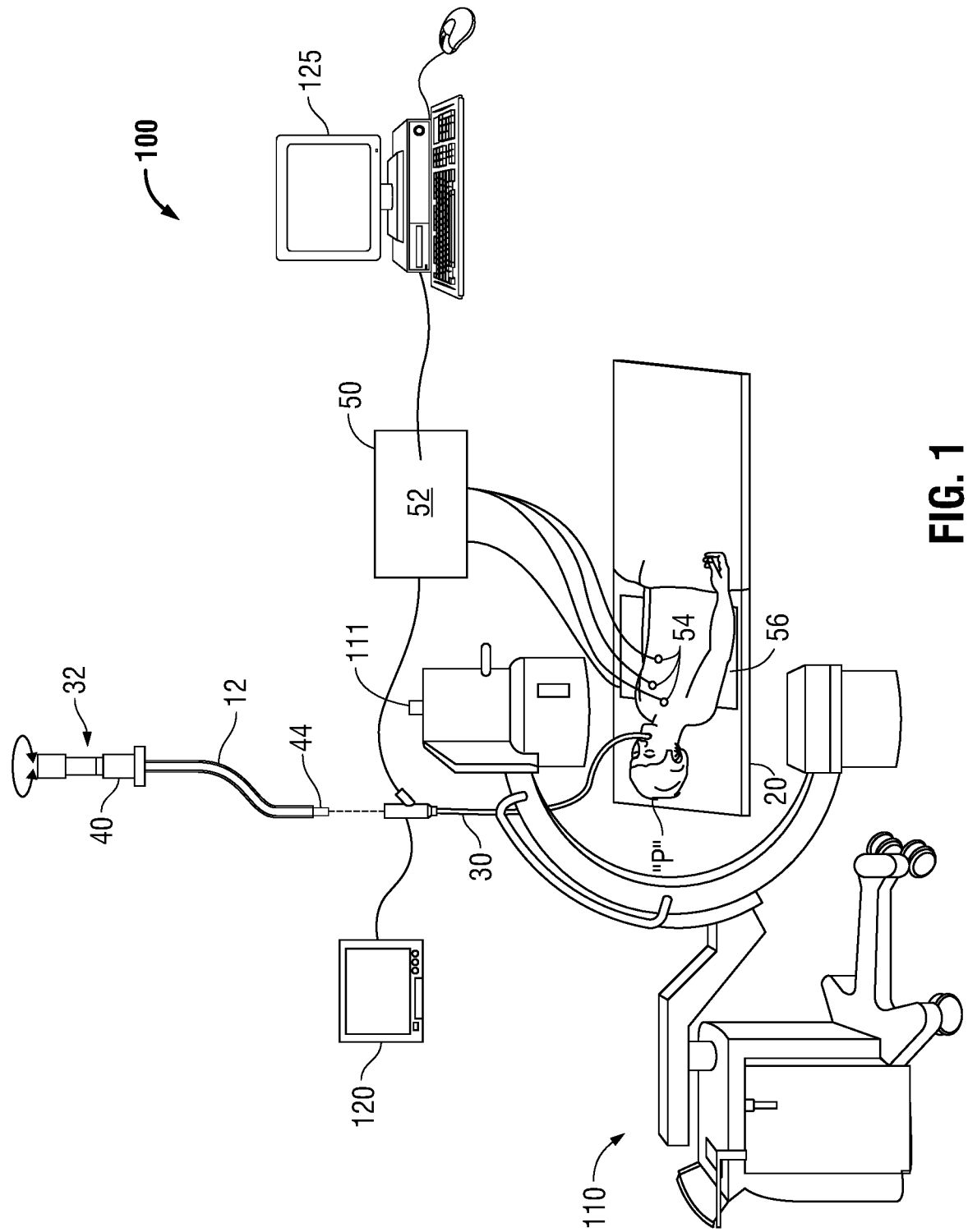
FIG. 1 is a perspective view of one illustrative embodiment of an electromagnetic navigation (EMN) system incorporating a fluoroscopic imaging device in accordance with the present disclosure.

FIG. 1 depicts an aspect of an Electromagnetic Navigation (EMN) system 100 configured for reviewing CT image data to identify one or more targets, planning a pathway to an identified target (planning phase), navigating an extended working channel (EWC) 12 of a catheter guide assembly 40 to a target (navigation phase) via a user interface, and confirming placement of the EWC 12 (or any portion of the catheter guide assembly 40 or any instruments inserted therethrough) relative to the target. One such electromagnetic navigation system is the ELECTROMAGNETIC NAVIGATION BRONCHOSCOPY® system currently sold by Medtronic PLC. The target may be tissue of interest or a region of interest identified during review of the CT image data during the planning phase. Following navigation, a medical instrument such as a biopsy tool, delivery device, or treatment device may be inserted into the EWC 12 to obtain a tissue sample from the tissue located at, or proximate to, the target, deliver items or therapies to the region, or treat the region.

Figure 2:
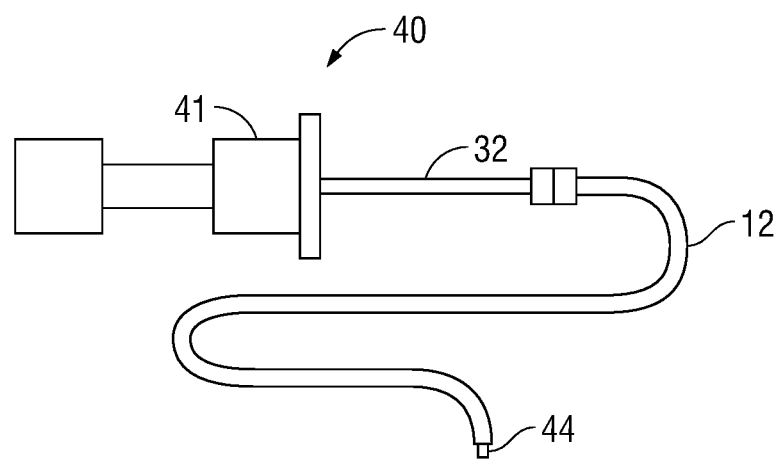
FIG. 2 is a perspective view of a catheter assembly usable with the system of FIG. 1.

As shown in FIGS. 1-2, EWC 12 is part of a catheter guide assembly 40 which extends distally from a handle 41 of the catheter guide assembly 40. In practice, the EWC 12 is inserted into bronchoscope 30 for access to a luminal network of the patient "P." Specifically, EWC 12 of catheter guide assembly 40 may be inserted into a working channel of bronchoscope 30 for navigation through a patient's luminal network. A locatable guide (LG) 32, including a sensor 44 disposed thereon, is inserted into the EWC 12 and locked into position such that the sensor 44 extends a desired distance beyond the distal tip of the EWC 12. The position and orientation of the sensor 44 relative to a reference coordinate system, and thus the distal end of the EWC 12, within an electromagnetic field can be derived. Catheter guide assemblies 40 are currently marketed and sold by Medtronic PLC under the brand names SUPERDIMENSION® Procedure Kits, or EDGE™ Procedure Kits, and are contemplated as useable with the present disclosure. For a more detailed description of the catheter guide assemblies 40, reference is made to commonly-owned U.S. Patent Publication No. 2014/0046315, filed on Mar. 15, 2013, by Ladtkow et al., U.S. Pat. Nos. 7,233,820, and 9,044,254, the entire contents of each of which are hereby incorporated by reference.

EMN system 100 generally includes an operating table 20 configured to support a patient "P;" a bronchoscope 30 configured for insertion through the patient "P's" mouth into the patient "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54 and a transmitter mat 56; and a computing device 125 including software and/or hardware used to facilitate identification of a target, pathway planning to the target, navigation of a medical instrument to the target, and confirmation of placement of an EWC 12, or a suitable device therethrough, relative to the target.

A fluoroscopic imaging device 110 capable of acquiring fluoroscopic or x-ray images or video of the patient "P" is also included in this particular aspect of system 100. The images, series of images, or video captured may be stored within the imaging device 110 or transmitted to computing device 125 for storage, processing, and display. Additionally, the fluoroscopic imaging device 110 may move relative to the patient "P" so that images may be acquired from different angles or perspectives relative to the patient "P" to create a fluoroscopic video. In one aspect of the present disclosure, fluoroscopic imaging device 110 includes an angle measurement device 111 which is configured to measure the angle of the fluoroscopic imaging device 110 relative to the patient "P." Angle measurement device 111 may be an accelerometer. Fluoroscopic imaging device 110 may include a single imaging device or more than one imaging device. In embodiments including multiple imaging devices, each imaging device may be a different type of imaging device or the same type. Further details regarding the fluoroscopic imaging device 110 are described in U.S. Pat. No. 8,565,858, which is incorporated by reference in its entirety herein.

Computing device 125 may be any suitable computing device including a processor and storage medium, wherein the processor is capable of executing instructions stored on the storage medium. The computing device 125 is operably coupled to some or all of the components of system 100 including bronchoscope 30, catheter guide assembly 40, locatable guide 32, and tracking system 50. The computing device 125 may include a database configured to store patient data, CT data sets including CT images and volumetric renderings, fluoroscopic data sets including fluoroscopic images and video, navigation plans, and any other such data. Although not explicitly illustrated, the computing device 125 may include inputs, or may otherwise be configured to receive, CT data sets, fluoroscopic images/video and other data described herein. Additionally, computing device 125 includes a display configured to display graphical user interfaces. Computing device 125 may be connected to one or more networks through which one or more databases may be accessed.

With respect to the planning phase, computing device 125 utilizes previously acquired CT image data for generating and viewing a three dimensional model of the patient's "P's" airways, enables the identification of a target on the three dimensional model (automatically, semi-automatically, or manually), and allows for determining a pathway through the patient's "P's" airways to tissue located at and around the target. More specifically, CT images acquired from previous CT scans are processed and assembled into a three dimensional CT volume, which is then utilized to generate a three dimensional model of the patient's "P's" airways. The three dimensional model may be displayed on a display associated with computing device 125, or in any other suitable fashion. Using computing device 125, various views of the three dimensional model or two dimensional images generated from the three dimensional model are presented. The three dimensional model may be manipulated to facilitate identification of target on the three dimensional model or two dimensional images, and selection of a suitable pathway through the patient's "P's" airways to access tissue located at the target can be made. Once selected, the pathway plan, three dimensional model, and images derived therefrom, can be saved and exported to a navigation system for use during the navigation phase(s). One such planning software is the ILOGIC® planning suite currently sold by Medtronic PLC.

With respect to the navigation phase, a six degrees-of-freedom electromagnetic tracking system 50, e.g., similar to those disclosed in U.S. Pat. Nos. 8,467,589, 6,188,355, and published PCT Application Nos. WO 00/10456 and WO 01/67035, the entire contents of each of which are incorporated herein by reference, or other suitable positioning measuring system, is utilized for performing registration of the images and the pathway for navigation, although other configurations are also contemplated. Tracking system 50 includes a tracking module 52, a plurality of reference sensors 54, and a transmitter mat 56. Tracking system 50 is configured for use with a locatable guide 32 and particularly sensor 44. As described above, locatable guide 32 and sensor 44 are configured for insertion through an EWC 12 into a patient "P's" airways (either with or without bronchoscope 30) and are selectively lockable relative to one another via a locking mechanism.

Transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. One or more of reference sensors 54 are attached to the chest of the patient "P." The six degrees of freedom coordinates of reference sensors 54 are sent to computing device 125 (which includes the appropriate software) where they are used to calculate a patient coordinate frame of reference. Registration, as detailed below, is generally performed to coordinate locations of the three dimensional model and two dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Further details of such a registration technique and their implementation in luminal navigation can be found in U.S. Patent Application Pub. No. 2011/0085720, the entire content of which is incorporated herein by reference, although other suitable techniques are also contemplated.

Registration of the patient "P's" location on the transmitter mat 56 is performed by moving LG 32 through the airways of the patient "P." More specifically, data pertaining to locations of sensor 44, while locatable guide 32 is moving through the airways, is recorded using transmitter mat 56, reference sensors 54, and tracking module 52. A shape resulting from this location data is compared to an interior geometry of passages of the three dimensional model generated in the planning phase, and a location correlation between the shape and the three-dimensional model based on the comparison is determined, e.g., utilizing the software on computing device 125. In addition, the software identifies non-tissue space (e.g., air filled cavities) in the three dimensional model. The software aligns, or registers, an image representing a location of sensor 44 with a the three-dimensional model and two-dimensional images generated from the three-dimension model, which are based on the recorded location data and an assumption that locatable guide 32 remains located in non-tissue space in the patient "P's" airways. Alternatively, a manual registration technique may be employed by navigating the bronchoscope 30 with the sensor 44 to pre-specified locations in the lungs of the patient "P", and manually correlating the images from the bronchoscope to the model data of the three dimensional model.

Following registration of the patient "P" to the image data and pathway plan, a user interface is displayed in the navigation software of system 100 which sets for the pathway that the clinician is to follow to reach the target. One such navigation software is the ILOGIC® navigation suite currently sold by Medtronic PLC.

Once EWC 12 has been successfully navigated proximate the target as depicted on the user interface, the locatable guide 32 may be unlocked from EWC 12 and removed, leaving EWC 12 in place as a guide channel for guiding medical instruments. Such medical instruments may include, without limitation, optical systems, ultrasound probes, marker placement tools, biopsy tools, ablation tools (i.e., microwave ablation devices), laser probes, cryogenic probes, sensor probes, and aspirating needles to the target.

The three dimensional model of a patient's lungs, generated from previously acquired CT scans, may not provide a basis sufficient for accurate guiding of the EWC 12 of the catheter guide assembly 40 to a target during the procedure. As described above, the inaccuracy may be caused by CT-to-Body divergence (deformation of the patient's lungs during the procedure relative to the lungs at the time of the acquisition of the previously acquired CT data). Thus, another imaging modality is necessary to visualize targets and/or a terminal bronchial branch, and enhance the electromagnetic navigation procedure by correcting the navigation during the procedure, enabling visualization of the target, and confirming placement of the surgical device during the procedure. For this purpose, the system described herein processes and converts image data captured by the fluoroscopic imaging device 110, as will be described in detail below. This fluoroscopic image data may be utilized to identify such targets and terminal bronchial branches or be incorporated into, and used to update, the data from the CT scans in an effort to provide a more accurate/correction of the electromagnetic navigation procedure. Further, the fluoroscopic images may be captured post-navigation and thus includes visuals of the EWC 12 and any medical devices positioned therethrough relative to the target.

Figure 3:
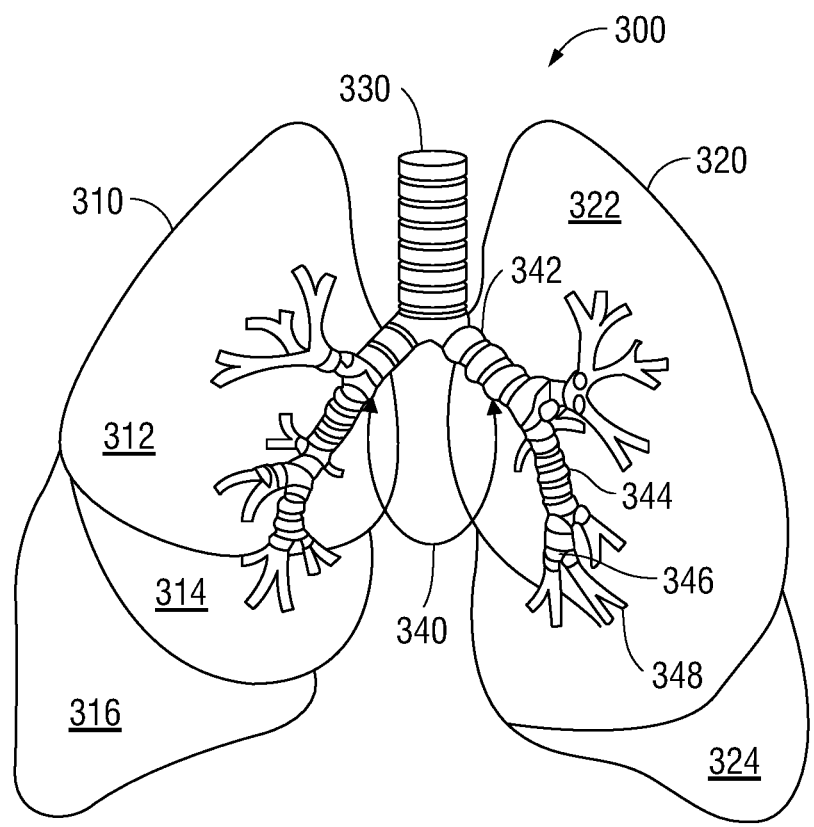
FIG. 3 is an anatomical illustration of a three dimensional model for a lung in accordance with an embodiment of the present disclosure.

FIG. 3 illustrates a three dimensional model 300 of a patient's bronchial tree and the trachea together with the lung. As described above, the three dimensional model may be a three dimensional rendering derived from CT data acquired from a previous CT scan. The three dimensional model 300 may include information of most of the organs so that a clinician may selectively see particular organs or portions of organs of interest as shown in FIG. 3. In this case, these selected organs are the lungs including right lung 310, left lung 320, trachea 330, and bronchial tree 340. The right lobe 310 has three sub-lobes, i.e., superior lobe 312, middle lobe 314, and inferior lobe 316, and the left lobe 320 has two sub-lobes, i.e., superior lobe 322 and inferior lobe 324.

The trachea 330 is a tube that connects the pharynx and larynx to the right and left lungs 310 and 320. At the lower end of the trachea 330, divides into the left and right primary bronchi 342 divides. The primary bronchi 242 divide into secondary bronchi 344 at its lower end. The circumference of the primary bronchus 342 is greater than that of the secondary bronchus 344. In the same manner, tertiary bronchus 346 divides at the lower end of the secondary bronchus 344 and terminal bronchiole 348 divides at the lower end of the tertiary bronchus 346. The primary bronchus 342, the secondary bronchus 344, and the tertiary bronchus 346 are supported by cartilaginous plates. However, as the size of the tertiary bronchus 346 becomes smaller, the cartilaginous plates disappear and outer wall is dominated by smooth muscle. The outer wall of the terminal bronchiole 348 is also dominated by smooth muscle.

Diseased or cancerous cells, or simply a target, may exist on any bronchial trees 340, the primary bronchus 342, the secondary bronchus 344, the tertiary bronchus 346, and the terminal bronchioles 348. In many instances, there is a delay in time between acquisition of the CT data for planning a procedure and the actual procedure itself. During this time, it is possible for targets to change in size and even for new targets to form. Utilizing a fluoroscopic-based local three dimensional reconstruction of the area of interest during the procedure phase provides greater specificity and greater accuracy in detecting and identifying a target's location relative to a navigated catheter guide assembly 40 in the patient.

In accordance with at least one embodiment, the fluoroscopic-based local three dimensional reconstruction of the area of interest is employed to update the image data of the lungs (three dimensional model 300) by following the pathway plan described above and capturing a fluoroscopic rotation video of the area of interest when the EWC 12 is navigated to the target. This fluoroscopic-based local three dimensional reconstruction may be registered to the CT scan images and/or the three dimensional model 300 to update the CT scan images and/or the three dimensional model with respect to the presence, location, and size of a target. In one aspect, this data may be used to visualize the target(s). Further, the data may also be used diagnostically to help the clinician confirm that all likely targets have been identified or treated completely after treatments. Additionally, the fluoroscopic-based local three dimensional reconstruction is generated after EWC 12 is navigated and thus includes visuals of the EWC 12 and any medical devices positioned therethrough relative to the target. Such data may be useful in assisting to confirm placement of the medical devices, preventing pneumothorax, and other benefits described herein. Additionally, the fluoroscopic-based local three dimensional reconstruction may be utilized in order to correct the electromagnetic navigation coordinates of the EWC 12 which may be inaccurately represented to the user due to C-to-Body divergence or deformation.

Figure 4A:
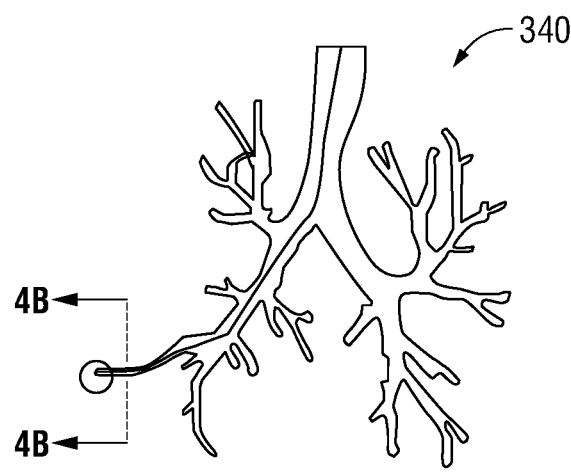
FIG. 4A is an illustration of a pathway from the entry point to the target in accordance with an embodiment of the present disclosure.

FIG. 4A shows a planar view of bronchial trees 340 of the three dimensional model or of the slices of images of the lung such as the bronchial trees of FIG. 3 and a pathway plan to a target. When a target is located at the distal regions of the bronchial tree 340 of FIG. 3, a pathway plan shows how to navigate to the target via the luminal network of the lung.

Figure 4B:
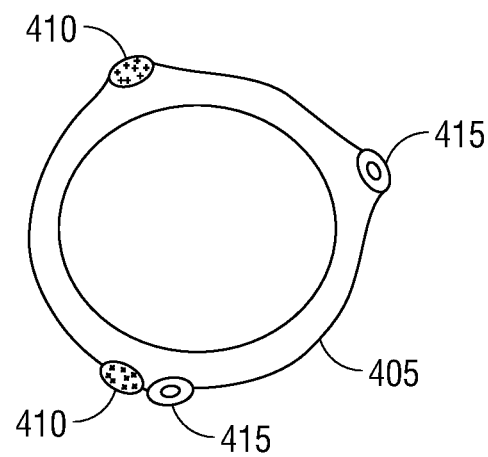
FIG. 4B is a transverse cross-sectional view of the section of the lung of FIG. 4A taken along section line B-B.

FIG. 4B shows an expanded transverse cross-sectional view of the terminal bronchiole of FIG. 4A taken along section line B-B. The terminal bronchiole is surrounded by smooth muscle 405. Nerves 410 and veins 415 are located on the outer wall of the smooth muscle 405. The fluoroscopic-based local three dimensional reconstruction, as described above, provides a local view of the airways, even out to the terminal bronchiole, so that when navigating to these peripheral regions, the position of the EWC 12 can be corrected or updated to cure any inaccuracies caused by CT-to-Body divergence. Thus, by using real time fluoroscopic imaging in addition to the previously acquired CT data, navigation to, and direction of, therapies such as denervation can be accomplished even at the lung periphery enabling greater granularity of treatment options, with greater precision, and with a better understanding of the anatomy that with the previously acquired CT data alone.

Figure 4C:
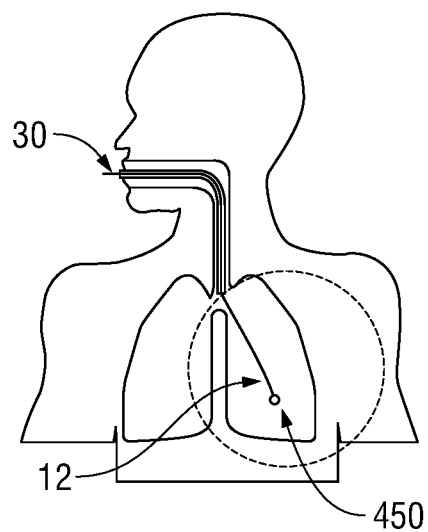
FIG. 4C is an illustration of a catheter guide assembly inserted into a lung following the pathway plan of FIG. 4A.
Figure 4D:
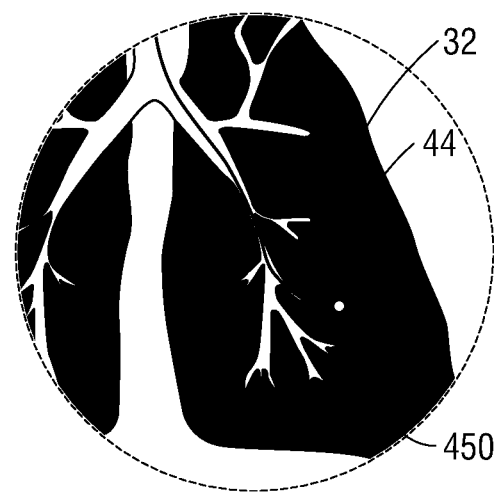
FIG. 4D is an enlarged detail view of the circled area of FIG. 4C.

FIG. 4C and FIG. 4D illustrate a bronchoscope 30 with a catheter guide assembly 40 inserted into the lungs via a natural orifice (e.g., the mouth) of a patient toward the target 450 following a pathway plan. When the bronchoscope 30 reaches a certain location of the lung, the bronchoscope 30 becomes wedged and cannot go further into bronchial tree due to the size constraints. Then, the EWC 12 of the catheter guide assembly 40 may be used to navigate the luminal network to a target 450 following the pathway plan, as described above. FIG. 4D illustrates an enlarged detail view of the circled area of FIG. 4C, where a sensor 44 of a locatable guide (LG) 32 may stick out of the distal tip of the EWC 12 which navigates the luminal network to the target 450 located at the terminal bronchiole of the lung.

Figure 5:
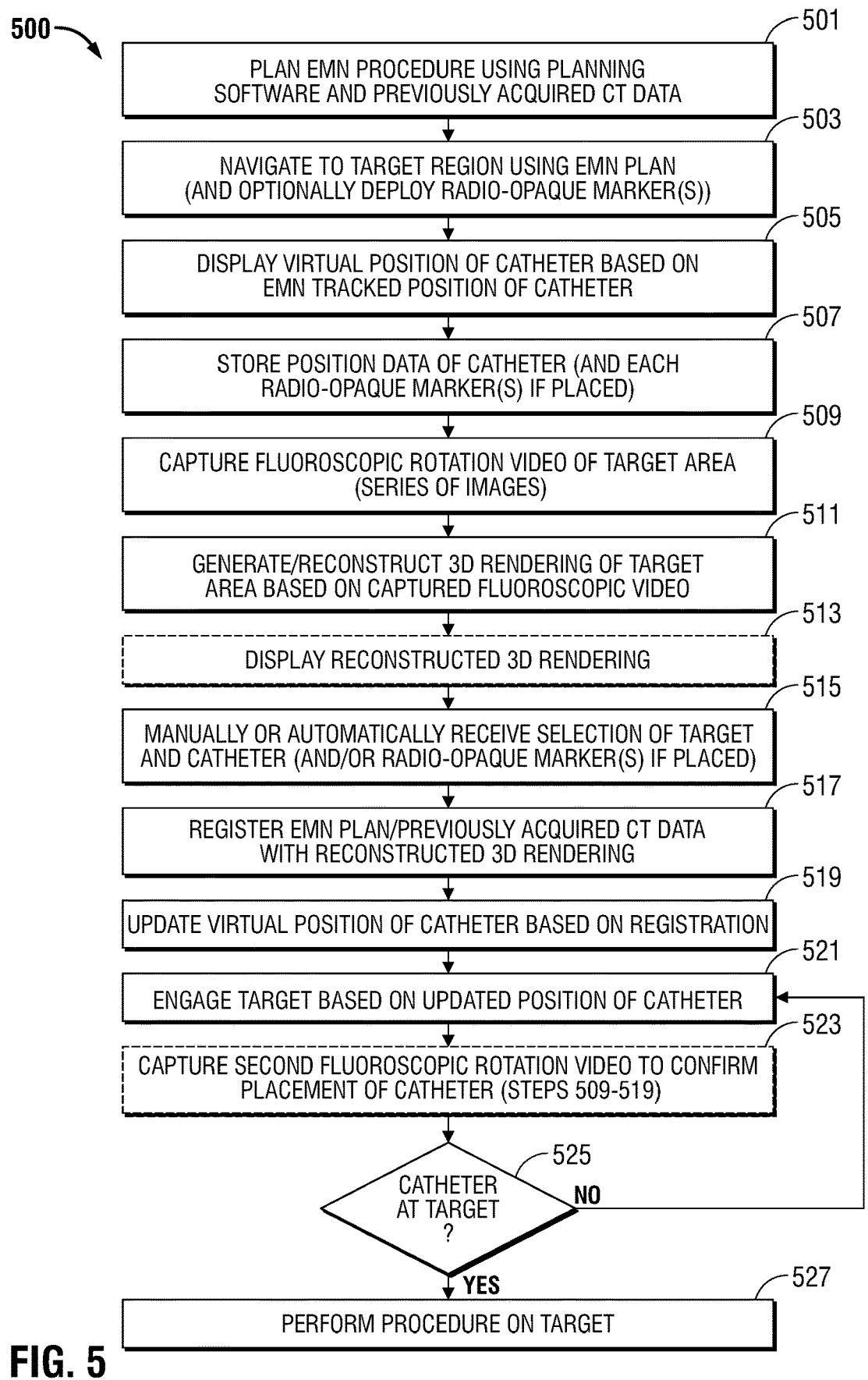
FIG. 5 is a flow chart of a method for navigating a catheter to a target.

Having described the components of system 100 depicted in FIGS. 1-2, the following description of FIG. 5 provides an exemplary workflow of using the components of system 100, including the fluoroscopic imaging device 110, to navigate through a luminal network of a patient utilizing a previously generated navigation plan and three-dimensional volumetric data of a desired region of interest generated from data received from the fluoroscopic imaging device 110 of system 100. The systems and methods described herein may be useful for visualizing a particular target region of a patient utilizing imaging devices which are commonly located within a surgical setting during EMN procedures and which expose the patient to less radiation than additional MRI and CT scans.

Although the methods illustrated and described herein are illustrated and described as being in a particular order and requiring particular steps, any of the methods may include some or all of the steps and may be implemented in any order not specifically described.

Turning now to FIG. 5, a method for enhanced navigation during an EMN procedure using fluoroscopic based three-dimensional volumetric data of a local region of a patient will now be described and referred to as method 500. Method 500 begins at step 501 where the EMN procedure is planned using planning software described above. In particular, previously acquired CT data is utilized to identify targets and plan navigation pathways to the targets.

In step 503, the navigation procedure begins where a portion of a catheter guide assembly is navigated to a target area utilizing an electromagnetic navigation system, such as the EMN system 100 (FIG. 1) described above. The navigation of the catheter guide assembly in step 503 may additionally include navigation of a marker placement device to the target area via the catheter guide assembly. As described above, the navigation in step 503 is accomplished using a previously created navigation plan which includes routes created during the planning phase. Step 503, may additionally include the step of placing radio-opaque markers within the target area. In one example, four radio-opaque markers are utilized. However, less than four or more than four radio-opaque markers may be used.

In step 505 the virtual position of the catheter guide assembly is displayed on the user interface of system 100. The virtual position of the catheter guide assembly is based on the electromagnetically tracked location of the catheter guide assembly within the patient's body. Throughout the entire navigation procedure, like in step 505, the virtual position of the catheter guide assembly is displayed on a user interface of system 100 to assist in navigating the EWC to the target. In step 507, the electromagnetically-tracked position data of the catheter guide assembly is stored in system 100. In instances where radio-opaque markers are placed within the region of the target, step 507 may additionally include the step of storing the location data of the catheter guide assembly at the time that each of the radio-opaque markers is placed. System 100 then identifies the position of each placed marker as the corresponding position of the catheter guide assembly at the time of deployment of the marker.

In step 509, with the catheter guide assembly navigated (and the radio-opaque markers placed in the target area, if placed), the fluoroscopic imaging device of system 100 is positioned such that the catheter guide assembly (and all of the radio-opaque markers, if placed) are visible in at least two different angles of the fluoroscopic imaging device relative to the patient. The fluoroscopic imaging device is then used to capture a video about the region of interest, that is the region where the catheter guide assembly is navigated to (and where the radio-opaque markers are located, if placed). In one aspect, the captured video may be of about a 30° rotation around the region of interest. However, less that, or more than, a 30° rotation may be utilized.

In step 511, a fluoroscopic-based local three dimensional volume is constructed from the captured fluoroscopic rotation video. Further details regarding exemplary techniques utilized to construct the local three dimensional volume from the captured fluoroscopic video may be found in U.S. Provisional Application Ser. No. 62/201,750, filed on Aug. 6, 2015, the entire content of which is incorporated by reference herein.

In step 513, the fluoroscopic-based local three dimensional volume generated in step 511 may optionally be displayed on a user interface of system 100. Because the fluoroscopic rotation video is captured after navigation of the EWC, and after placement of any markers, the catheter guide assembly (and the radio-opaque markers, if placed) are included in the fluoroscopic images/video and are visible in the display of the fluoroscopic-based three dimensional volume. In one aspect, the display of the fluoroscopic-based local three dimensional volume in step 513 is carried out by projecting the fluoroscopic-based local three dimensional volume (or a localized portion thereof) back onto the two dimensional images captured in the fluoroscopic video from step 509. For example, step 513 may include projecting the generated fluoroscopic-based local three dimensional volume of the target area onto the two dimensional fluoroscopic images used to create the three dimensional volume for at least two different angles. Such a projection provides confirmation that the catheter or EWC is in, or is not in, the target area in both of the two different angles. Such a display as described above can also enable marking the catheter or EWC and target on both two dimensional images to obtain the relative three dimensional position of the catheter or EWC and target. These capabilities are enabled because projecting the target area provides a greater detail of the density differences in the target area, without obstruction of much denser objects (such as ribs, spine, heart, fat, major By, etc.). Thus, the soft tissue objects, such as a target lesion, can be observed in this manner. Such marking may be accomplished manually by a user via the user interface or automatically by the system, for example by image analysis. This relative position may be utilized to correct the position on the previously acquired CT data.

In step 515, a selection of the image of the catheter guide assembly (and the radio-opaque markers, if placed) from the fluoroscopic-based local three dimensional volume is made. Step 515 may be implemented in a variety of ways. In one aspect, a clinician may select, or otherwise outline, the catheter guide assembly or markers from the display of step 513. In another aspect, system 100 may perform an image analysis of the fluoroscopic-based local three dimensional volume and determine the location of the catheter guide assembly and markers within the three dimensional volume. In another aspect, the system 100 may suggest the detected catheter and markers and present the suggestion to a clinician for approval/modification of the system's suggestion.

In step 517, the previously acquired CT data or the previously generated navigation plan is registered with the fluoroscopic-based local three dimensional volume which has been reconstructed in step 511. With the virtual location of the catheter assembly known based on the electromagnetic field generated and sensed, in step 519, the displayed virtual location of the catheter assembly is updated, or otherwise corrected, based on the newly registered data from step 517. In particular, in step 519, the position of the catheter assembly is more accurately depicted based on the registration of the fluoroscopic-based local three dimensional volume with the previously acquired CT data.

In step 521, the clinician further advances the catheter assembly to engage the target utilizing the updated and more accurate position data of the catheter assembly displayed on the display. In step 523, subsequent to the clinician repositioning the catheter assembly in step 521, a second fluoroscopic rotation video may be captured if desired. Step 523 is similar to any, or all, of steps 509-519 and will not be described in further detail. Upon capturing a second fluoroscopic video in step 523, the system may present the clinician with a more accurate position and location of the catheter guide assembly after the catheter guide assembly has been repositioned in step 521.

In step 525 it is determined if the catheter guide assembly is at the target. In one aspect, step 525 is accomplished by determining whether a distance between a portion of the catheter guide assembly and an edge, or center, of the target is within a predetermined threshold. When the distance between the catheter guide assembly and the target is more than the predetermined threshold, then it is determined that the catheter guide assembly is not at the target (no in step 525) and method 500 reverts to step 521 where the clinician can adjust the position of the catheter guide assembly. When the distance between the catheter guide assembly and the target is less than the predetermined threshold, then it is determined that the catheter guide assembly is at the target (yes in step 525) and method 500 proceeds to step 527.

In step 527, the procedure is performed on the target. As described above, method 500 may be used to navigate to a target region for various purposes. That is, step 527 may include any type of procedure, which may include for example, biopsy collection, marker placement, device placement, therapeutic treatments, agent delivery, ablation treatments including radiofrequency and microwave ablations, and any other such procedure that may benefit from enhanced and more accurate navigation through a luminal network.

From the foregoing and with reference to the various figure drawings, those skilled in the art will appreciate that certain modifications can also be made to the present disclosure without departing from the scope of the same.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and the present disclosure is directed to systems and methods that are usable with such instruments and tools. Access to luminal networks may be percutaneous or through natural orifice using navigation techniques. Additionally, navigation through a luminal network may be accomplished using image-guidance. These image-guidance systems may be separate or integrated with the energy device or a separate access tool and may include MRI, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device or tool placement may be performed with imaging and/or navigational guidance using a standard fluoroscopic imaging device incorporated with methods and systems described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for navigating to a target area within an organ using fluoroscopic-based three-dimensional volumetric data generated from two-dimensional fluoroscopic images, comprising:
   a medical device configured to be navigated through the organ to a target of the organ within the target area; and
   a computing device configured to:
   receive previously acquired CT data;
   generate a CT-based three-dimensional rendering of the target area of a patient based on the previously acquired CT data;
   determine a location of the medical device;
   receive a series of fluoroscopic images of the target area captured by a fluoroscopic imaging device;
   display the location of the medical device relative to the CT-based three-dimensional rendering of the patient;
   determine poses of the fluoroscopic imaging device corresponding to a plurality of fluoroscopic images of the series of fluoroscopic images;
   generate a fluoroscopic-based three-dimensional reconstruction of the target area based on the series of fluoroscopic images of the target area captured by the fluoroscopic imaging device and the poses determined;
   receive a selection of the medical device from at least one of the fluoroscopic-based three-dimensional reconstruction of the target area or at least two fluoroscopic images of the series of fluoroscopic images;
   receive a selection of the target from at least one of the fluoroscopic-based three-dimensional reconstruction of the target area or at least two fluoroscopic images of the series of fluoroscopic images;
   determine a position of the medical device relative to the target in the target area within the fluoroscopic-based three-dimensional reconstruction; and
   update the location of the medical device displayed relative to the CT-based three-dimensional rendering of the patient based on the position of the medical device relative to the target in the target area within the fluoroscopic-based three-dimensional reconstruction of the target area.

2. The system according to claim 1, wherein the computing device is further configured to receive the selection of the target located in the target area from the fluoroscopic-based three-dimensional reconstruction.

3. The system according to claim 1, wherein the computing device is configured to receive the selection of the target by:
    automatically detecting a portion of the target in at least one of the fluoroscopic-based three-dimensional reconstruction or at least two fluoroscopic images of the series of fluoroscopic images;
    presenting the detection to a user; and
    receiving a user command either accepting or rejecting the detection.

4. The system according to claim 1, wherein the computing device is configured to receive the selection of the medical device by:
    automatically detecting a portion of the medical device in at least one of the fluoroscopic-based three-dimensional reconstruction or at least two fluoroscopic images of the series of fluoroscopic images;
    presenting the detection to a user; and
    receiving a user command either accepting or rejecting the detection.

5. The system according to claim 1, wherein the poses of the fluoroscopic imaging device are determined based on an external angle measuring device coupled to the fluoroscopic imaging device.

6. A method for navigating through an organ to a target of a target area within the organ using fluoroscopic-based three-dimensional volumetric data generated from two-dimensional fluoroscopic images, comprising:
    receiving previously acquired CT data;
    generating a CT-based three-dimensional rendering of the target area of a patient based on the previously acquired CT data;
    determining a location of a medical device navigated to the target area;
    displaying the location of the medical device relative to the CT-based three-dimensional rendering of the patient;
    receiving a series of fluoroscopic images of the target area about a plurality of angles relative to the target area captured by a fluoroscopic imaging device;
    determine poses of the fluoroscopic imaging device corresponding to a plurality of fluoroscopic images of the series of fluoroscopic images;
    generating a fluoroscopic-based three-dimensional reconstruction of the target area based on the series of fluoroscopic images of the target area received and the poses determined;
    receiving a selection of the medical device from at least one of the fluoroscopic-based three-dimensional reconstruction or at least two fluoroscopic images of the series of fluoroscopic images;
    determining a position of the medical device relative to the target in the target area within the fluoroscopic-based three-dimensional reconstruction; and
    updating the location of the medical device displayed relative to the CT-based three-dimensional rendering of the patient based on the position of the medical device relative to the target in the target area within the fluoroscopic-based three-dimensional reconstruction of the target area.

7. The method according to claim 6, further comprising receiving a selection of the target located in the target area from at least one of the fluoroscopic-based three-dimensional reconstruction or at least two fluoroscopic images of the series of fluoroscopic images.

8. The method according to claim 7, wherein receiving the selection of the target includes:
    automatically detecting a portion of the target in at least one of the fluoroscopic-based three-dimensional reconstruction or at least two fluoroscopic images of the series of fluoroscopic images;
    presenting the detection to a user; and
    receiving a user command either accepting or rejecting the detection.

9. The method according to claim 6, wherein receiving the selection of the medical device includes:
    automatically detecting a portion of the medical device in at least one of the fluoroscopic-based three-dimensional reconstruction or at least two fluoroscopic images of the series of fluoroscopic images;
    presenting the detection to a user; and
    receiving a user command either accepting or rejecting the detection.

10. The method according to claim 6, further comprising tracking a two dimensional position or orientation of the medical device navigated to the target area throughout the series of fluoroscopic images.

11. The method according to claim 6, wherein the poses are determined based on an external angle measuring device coupled to the fluoroscopic imaging device.

12. A non-transitory computer readable storage medium, storing instructions which when executed by a processor, cause the processor to perform a method for navigating through an organ to a target of a target area within the organ using fluoroscopic-based three-dimensional volumetric data generated from two-dimensional fluoroscopic images, the method comprising:
    receiving previously acquired CT data;
    generating a CT-based three-dimensional rendering of the target area of a patient based on the previously acquired CT data;
    determining a location of medical device;
    displaying the location of the medical device relative to the CT-based three-dimensional rendering of the patient;
    receiving a series of fluoroscopic images of the target area about a plurality of angles relative to the target area captured by a fluoroscopic imaging device;
    generating a fluoroscopic-based three-dimensional reconstruction of the target area based on the series of fluoroscopic images of the target area;
    receiving a selection of the medical device from at least one of the fluoroscopic-based three-dimensional reconstruction or at least two fluoroscopic images of the series of fluoroscopic images;
    determining a position of the medical device relative to the target in the target area within the fluoroscopic-based three-dimensional reconstruction; and
    updating the location of the medical device displayed relative to the CT-based three-dimensional rendering of the patient based on the position of the medical device relative to the target in the target area within the fluoroscopic-based three-dimensional reconstruction of the target area.

13. The non-transitory computer readable storage medium according to claim 12, wherein the method further comprises receiving a selection of the target located in the target area from at least one of the fluoroscopic-based three-dimensional reconstruction or at least two fluoroscopic images of the series of fluoroscopic images.

14. The non-transitory computer readable storage medium according to claim 13, wherein receiving the selection of the target includes:
- automatically detecting a portion of the target in at least one of the fluoroscopic-based three-dimensional reconstruction or at least two fluoroscopic images of the series of fluoroscopic images;
- presenting a user with the detection; and
- receiving a user command either accepting or rejecting the detection.

15. The non-transitory computer readable storage medium according to claim 12, wherein receiving the selection of the medical device includes:
- automatically detecting a portion of the medical device in at least one of the fluoroscopic-based three-dimensional reconstruction or at least two fluoroscopic images of the series of fluoroscopic images;
- presenting a user with the detection; and
- receiving a user command either accepting or rejecting the detection.

16. The non-transitory computer readable storage medium according to claim 12, wherein the method further comprises determining a pose of the fluoroscopic imaging device for each frame of the series of fluoroscopic images.

* * * * *